US00PP11397P

United States Patent [19]

Trees

[11] Patent Number: Plant 11,397

[45] Date of Patent: May 30, 2000

[54] GERANIUM PLANT NAMED 'BFP-1700'

[75] Inventor: Scott C. Trees, Nipomo, Calif.

[73] Assignee: Ball Floraplant a division of Ball Horticultural Co., West Chicago, Ill.

[21] Appl. No.: 09/114,056

[22] Filed: Jul. 10, 1998

[51] Int. Cl.[7] ..... A01H 5/00

[52] U.S. Cl. ..... Plt./325

[58] Field of Search ..... Plt./325, 326

*Primary Examiner*—Howard J. Locker
*Assistant Examiner*—Kent L. Bell
*Attorney, Agent, or Firm*—C. A. Whealy

[57] ABSTRACT

A new and distinct cultivar of Geranium plant named 'BFP-1700', characterized by its numerous semi-double white and dark pink bi-colored flowers; upright and rounded growth habit; vigorous and basal branching; and dark green leaves.

1 Drawing Sheet

BACKGROUND OF THE INVENTION

The present invention relates to a new and distinct cultivar of Geranium plant, botanically known as *Pelargonium×hortorum*, and hereinafter referred to by the cultivar name 'BFP-1700'.

The new Geranium is a product of a planned breeding program conducted by the Inventor in Arroyo Grande, Calif. The objective of the breeding program was to develop new cultivars with excellent basal branching, medium growth habit, numerous flowers and umbels, and interesting flower and foliage colors.

The new Geranium originated from a cross made by the Inventor of the *Pelargonium×hortorum* cultivar 'Ice Crystal' (not patented) as the male, or pollen parent, with the proprietary *Pelargonium×hortorum* selection 1203 as the female, or seed parent. The cultivar 'BFP-1700' was discovered and selected by the Inventor as a flowering plant within the progeny of the stated cross in a controlled environment in Arroyo Grande, Calif., on Sep. 15, 1996. Compared to plants of the cultivar 'Ice Crystal', plants of the new cultivar have stronger peduncles. In addition, petal bases of plants of the new cultivar are white whereas petal bases of plants of the cultivar 'Ice Crystal' are lavender in color.

Asexual reproduction of the new cultivar by terminal cuttings taken at Arroyo Grande, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'BFP-1700'. These characteristics in combination distinguish 'BFP-1700' as a new and distinct cultivar:

1. Numerous semi-double white and dark pink bi-colored flowers with white centers.
2. Upright and rounded growth habit.
3. Vigorous and basal branching.
4. Dark green leaves.

The new Geranium can be compared to the cultivar, 'Americana White Splash' (disclosed in U.S. Plant Pat. No. 9,317). However, in side-by-side comparisons conducted by the Inventor in Arroyo Grande, Calif., plants of the new Geranium differ from plants of the cultivar 'Americana White Splash' in the following characteristics:

1. Plants of the new Geranium are slightly larger than plants of the cultivar 'Americana White Splash'.
2. Plants of the new Geranium have slightly darker green leaves than plants of the cultivar 'Americana White Splash'.
3. Plants of the new Geranium have darker pink central spots on the flower petals than plants of the cultivar 'Americana White Splash'.

A detailed comparison of plants of the cultivar 'BFP-1700' and the cultivar 'Americana White Splash' appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical plant of 'BFP-1700'. Flower and foliage colors in the photograph may appear different from the actual colors due to light reflectance.

DETAILED BOTANICAL DESCRIPTION

The cultivar 'BFP-1700' has not been observed under all possible environmental conditions. The phenotype may vary somewhat with variations in environment such as temperature and light intensity, without, however, any variance in genotype. The following observations, measurements and comparisons describe plants grown in 10-cm pots in Arroyo Grande, Calif., under commercial practice in a glass-covered greenhouse with day temperatures about 22° C. and night temperatures about 18° C.

In the following description, color references are made to The Royal Horticultural Society Colour Chart except where general terms of ordinary dictionary significance are used.

Botanical classification: *Pelargonium×hortorum* cultivar 'BFP-1700'.

Parentage:

*Male parent.*—*Pelargonium×hortorum* cultivar 'Ice Crystal', not patented.

*Female parent.*—Proprietary *Pelargonium×hortorum* selection 1203.

Propagation:

*Type cutting.*—Terminal cuttings.

*Time to initiate roots.*—About 7 days with 18° C.

*Time to develop roots.*—About 21 days with 18° C.

*Rooting habit.*—Fibrous and freely branching.

Plant description:

*General appearance.*—Upright and rounded growth habit, vigorous. Appropriate for 10 and 12.5-cm containers. About nine weeks are required to produced a finished 10-cm container from a rooted cutting.

*Growth and branching habit.*—Basally branching with about three lateral branches at the base.

*Plant height base of plant to top of leaf plane.*—About 12.3 cm.

*Plant width.*—About 22.3 cm.

*Lateral branches.*—Length: About 4 cm. Internode length: About 7.5 mm. Color: 145A.

*Foliage description.*—Leaves simple, generally symmetrical, abundant, opposite. Quantity of leaves per lateral branch: About six. Length: About 6.5 cm. Width: About 9 cm. Shape: Reniform with rounded apex, cordate base, crenate and undulating margin. Texture: Leathery, both surfaces pubescent. Color: Fully expanded foliage, upper surface: 147A. Fully expanded foliage, lower surface: 147B. Venation, upper surface: 146B. Venation, lower surface: 146B. Petiole: Length: About 4.8 cm. Diameter: About 2.5 mm. Color: 146B.

Flower description:

*Flower type and habit.*—White and dark pink bi-colored flowers. Very freely and continuously flowering. Flowers arranged in hemispherical umbels arising from apical leaf axils. Umbels displayed above or beyond the foliage. Usually about five umbels per plant. Flowers semi-double, round, flat to slightly cupped. Umbels persistent.

*Flowering season.*—Year-round under greenhouse conditions. In the garden, flowering is continuous from spring through summer.

*Umbels.*—Number of flowers per umbel: About 29. Diameter: About 10 cm. Height: About 6.3 cm.

*Flowers.*—Diameter: About 4.5 cm. Depth (height): About 1 cm.

*Flower buds.*—Length: About 1.6 cm. Diameter: About 7 mm. Shape: Elliptic.

*Petals.*—Quantity: Typically 5 or 6 petals and one petaloid per flower overlapping. Length: About 2.9 cm. Width: About 2.3 cm. Shape: Obovate with rounded apex and entire margin. Texture: Satiny. Color: Fully opened, upper surface: White, 155D, with central dark pink, 57A, spot on each petal. Purple, 67A, venation apparent on upper petals. Under high light conditions, background color becomes light pink, 65D. Dark pink spot fading to 57D with subsequent development. Fully opened, lower surface: White, 155D, with central dark pink, 57A, spot on each petal. Purple, 67A, venation slightly apparent on upper petals. Under high light conditions, background color becomes light pink, 65D. Petaloids: Irregularly shaped with vary narrow bases; about 1.3 cm in length and about 4 mm in width; white, 155D, in color.

*Peduncle* (*umbel stem*):—Length: About 16.7 cm. Strength: Strong. Angle: Mostly erect. Texture: Pubescent. Color: 146B.

*Pedicel* (*individual flower stem*).—Length: About 4.3 cm. Texture: Pubescent. Color: 145A.

*Reproductive organs.*—Androecium: Anther size: About 2 mm. Amount of pollen: Moderate. Pollen color: 34A. Gynoecium: Ovary color: Green.

Disease resistance: Under commercial conditions, resistance to pathogens has not been observed.

Seed development: Seed production has not been observed.

CHART A

| CHARACTERISTIC | 'BFP-1700' | 'AMERICANA WHITE SPLASH' |
|---|---|---|
| PLANT HEIGHT | About 12.3 cm | About 11 cm |
| PLANT WIDTH | About 22.3 cm | About 21.5 cm |
| LATERAL BRANCH LENGTH | About 4 cm | About 4.6 cm |
| LEAF COLOR, UPPER SURFACE | 147A | Lighter than 147A |
| LEAF COLOR, LOWER SURFACE | 147B | 147C |
| PETAL COLOR, UPPER SURFACE | White, 155D, with central dark pink, 57A, spot | White, 155D, with central pink, 67C, spot |
| POLLEN COLOR | 34A | 32A |

It is claimed:

1. A new and distinct cultivar of Geranium plant named 'BFP-1700', as illustrated and described.

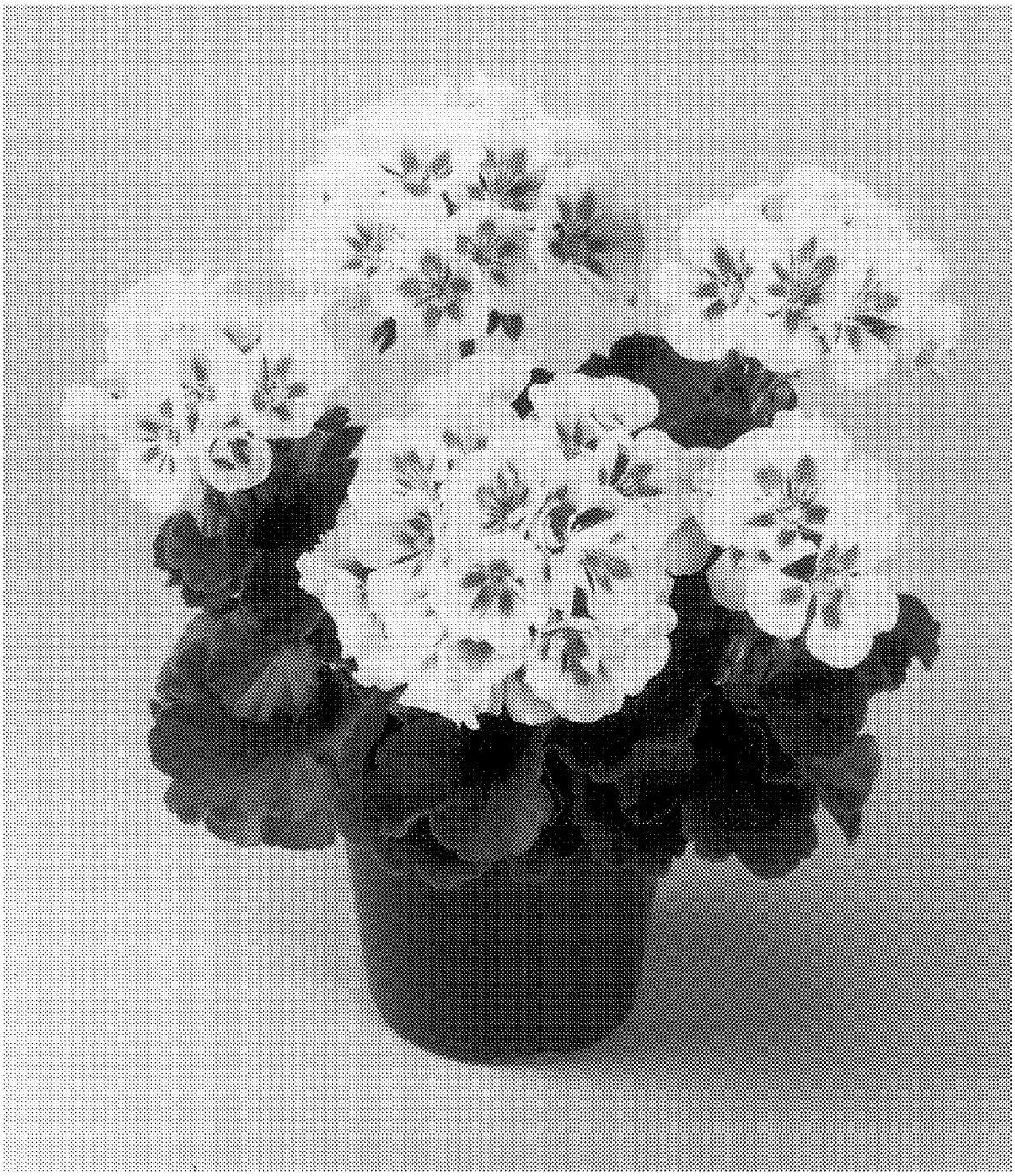

* * * * *